United States Patent
Vincent et al.

(10) Patent No.: US 11,170,889 B2
(45) Date of Patent: Nov. 9, 2021

(54) SMOOTH IMAGE SCROLLING

(71) Applicant: FUJIFILM MEDICAL SYSTEMS U.S.A., INC., Lexington, MA (US)

(72) Inventors: Brigil Vincent, Morrisville, NC (US); Tatsuo Kawanaka, Morrisville, NC (US); Maneesh Chirangattu, Morrisville, NC (US)

(73) Assignee: Fujifilm Medical Systems U.S.A., Inc., Lexington, MA (US)

( * ) Notice: Subject to any disclaimer, the term of this patent is extended or adjusted under 35 U.S.C. 154(b) by 0 days.

(21) Appl. No.: 16/248,437

(22) Filed: Jan. 15, 2019

(65) Prior Publication Data
US 2020/0227157 A1 Jul. 16, 2020

(51) Int. Cl.
| | | |
|---|---|---|
| *G16H 10/60* | (2018.01) | |
| *G16H 30/20* | (2018.01) | |
| *G06N 20/00* | (2019.01) | |
| *G06F 3/0482* | (2013.01) | |
| *G06F 3/0485* | (2013.01) | |

(52) U.S. Cl.
CPC .......... *G16H 30/20* (2018.01); *G06F 3/0482* (2013.01); *G06F 3/0485* (2013.01); *G06N 20/00* (2019.01); *G16H 10/60* (2018.01)

(58) Field of Classification Search
CPC ........ G16H 30/20; G16H 30/40; G16H 10/60; G06F 19/321; G06F 16/44; G06F 3/0482; G06F 3/0485; H04N 21/251; G06N 20/00
See application file for complete search history.

(56) References Cited

U.S. PATENT DOCUMENTS

| | | | | |
|---|---|---|---|---|
| 8,867,807 B1* | 10/2014 | Fram | ...................... | A61B 5/742 |
| | | | | 382/128 |
| 10,162,483 B1* | 12/2018 | Fram | ...................... | G06F 3/0236 |
| 10,395,762 B1* | 8/2019 | Fram | ...................... | G16H 30/40 |
| 2004/0077952 A1* | 4/2004 | Rafter | .................. | G06F 19/321 |
| | | | | 600/481 |
| 2006/0093207 A1* | 5/2006 | Reicher | ............... | G06F 3/04845 |
| | | | | 382/156 |
| 2008/0069397 A1* | 3/2008 | Bartsch | ................. | G06F 19/321 |
| | | | | 382/100 |
| 2009/0012821 A1* | 1/2009 | Besson | ................. | G06Q 50/24 |
| | | | | 705/3 |
| 2009/0182577 A1* | 7/2009 | Squilla | .................... | G06Q 50/22 |
| | | | | 705/2 |
| 2011/0238618 A1* | 9/2011 | Valdiserri | .............. | G16H 40/63 |
| | | | | 707/608 |

(Continued)

*Primary Examiner* — Eileen M Adams
(74) *Attorney, Agent, or Firm* — Heslin Rothenberg Farley & Mesiti P.C.

(57) ABSTRACT

A system and method for performing smooth image scrolling are disclosed. In one embodiment, the system comprises: a network communication interface to receive images of a healthcare study; an image cache memory to cache the images; one or more processors coupled to the network connection interface and the memory and configured to dynamically change playback behavior for navigating through images of the healthcare study based on analyzing historical user inputs made with one or more user input devices while a user is navigating through the images; and a display coupled to the one or more processors to display the images in a viewport.

20 Claims, 7 Drawing Sheets

(56) References Cited

U.S. PATENT DOCUMENTS

| | | | | |
|---|---|---|---|---|
| 2012/0095953 A1* | 4/2012 | Schmidt | ............... | G06N 20/00 |
| | | | | 706/52 |
| 2012/0154431 A1* | 6/2012 | Fram | ................. | G06F 3/0483 |
| | | | | 345/619 |
| 2014/0063219 A1* | 3/2014 | Stonefield | ............ | G16H 40/63 |
| | | | | 348/77 |
| 2014/0282636 A1* | 9/2014 | Petander | ............ | H04N 21/422 |
| | | | | 725/1 |
| 2015/0331995 A1* | 11/2015 | Zhao | ................. | G16H 40/63 |
| | | | | 705/2 |
| 2016/0071547 A1* | 3/2016 | Sugawara | ............ | G06Q 50/24 |
| | | | | 386/241 |
| 2017/0053064 A1* | 2/2017 | Bhavani | .............. | G06Q 50/22 |
| 2018/0075188 A1* | 3/2018 | Reicher | ............. | G06F 3/04845 |
| 2018/0268110 A1* | 9/2018 | Huynh | ............. | H04N 5/23296 |
| 2018/0310047 A1* | 10/2018 | Duan | ............... | H04N 21/4392 |
| 2019/0005263 A1* | 1/2019 | Holl | .................. | G16H 40/63 |

* cited by examiner

Learning Engine
[1.1] Receive input from user
[1.2] Store inputs to input history
[1.3] Notify input arrival to learning engine
[1.4] Fetch historical inputs
[1.5] Update playback behavior Image Loader
[2.1] Fetch playback behavior
[2.2] WADO request to imaging service
[2.2] Cache displayable images Playback Engine
[3.1, 3.2] Synchronize user inputs and playback engine
[3.3] Fetch playback behavior
[3.4] Fetch displayable image from cache
[3.5] Draw image in viewport

FIG. 4

SMOOTH IMAGE SCROLLING

FIELD OF THE INVENTION

Embodiments of the present invention relate to the field of viewing medical images; more particularly, embodiments of the present invention relate to changing the navigation of medical images dynamically while a user is viewing the images.

BACKGROUND

Current medical imaging technology includes the use of medical images such as, among others, x-rays, mammograms, computerized tomography (CT) scans, magnetic resonance images (MRIs), positron emission tomography (PET) scans and ultrasound images. These images are generated by medical imaging modalities.

Medical facilities are more readily adopting electronic displays for displaying medical images. The medical images are often Digital Imaging and Communications in Medicine (DICOM) images. Often after an imaging modality takes medical images, those images are included in a study that is sent to a picture archiving and communication system (PACS). The PACS is a medical imaging technology that allows access to images from multiple locations. Doctors and/or other medical professionals obtain studies that are stored in the PACS and review, or read, the images in the studies to obtain clinical information about their patients. If a patient has a serious medical condition that needs urgent attention, the doctor is often able to make that determination by reviewing the images in the study.

Doctors and/or other medical professionals often view the images on workstation that has a display. To view the images from a study on the workstation, the images are rendered at a remotely-located server and then the rendered images are downloaded through a network for display on the workstation. The rendering of a particular image occurs in real-time in response to a request to view the image.

When reviewing DICOM images to locate anatomies and lesions, it is essential that the navigation through the DICOM images is seamless. Cine images are viewed as movies that illustrate the motion of a patient's heart and can be obtained via segmented imaging. Current methods of cine playback are not suitable for quickly change navigation speed and direction as radiologist navigate through the DICOM images. Also, current manual scrolling mechanisms are not suitable for changing navigation speed smoothly when scrolling through anatomies.

SUMMARY OF THE INVENTION

A system and method for performing smooth image scrolling are disclosed. In one embodiment, the system comprises: a network communication interface to receive images of a healthcare study; an image cache memory to cache the images; one or more processors coupled to the network connection interface and the memory and configured to dynamically change playback behavior for navigating through images of the healthcare study based on analyzing historical user inputs made with one or more user input devices while a user is navigating through the images; and a display coupled to the one or more processors to display the images in a viewport.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 4 illustrates an operations list for a learning engine, an image loader and a playback engine for one embodiment of a medical image management system.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Embodiments of the present invention are directed to systems, methods, and GUIs for rendering and displaying medical, or healthcare, images. The systems, methods, and GUIs of the present invention provide seamless navigation through images, such as those, for example, found in healthcare studies or series. In one embodiment, these images are DICOM multi-frame or non-multiform images of a study or series. The techniques disclosed herein allow a radiologist to control or change navigation behavior on the fly. Having briefly described an overview of the present invention, embodiments of the invention will be discussed with reference to FIGS. 1-7.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
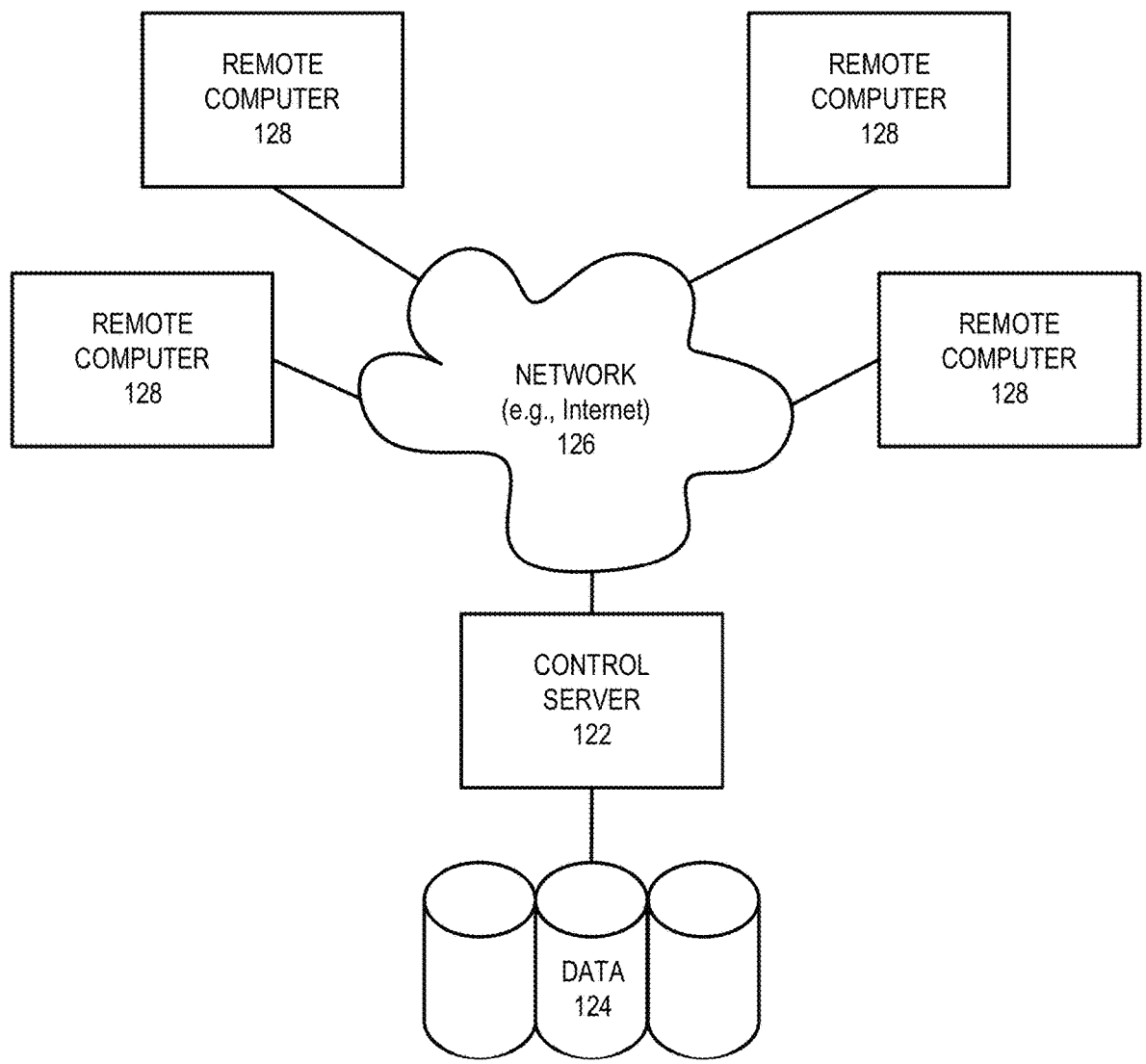
FIG. 1 illustrates an exemplary a medical information computing system environment, with which embodiments of the present invention may be implemented.

Referring to the drawings in general, and initially to FIG. 1 in particular, a medical information computing system environment, with which embodiments of the present invention may be implemented is illustrated and designated generally as reference numeral 120. It will be understood and appreciated by those of ordinary skill in the art that the illustrated medical information computing system environment 120 is merely an example of one suitable computing environment and is not intended to suggest any limitation as to the scope of use or functionality of the invention. Neither should the medical information computing system environment 120 be interpreted as having any dependency or requirement relating to any single component or combination of components illustrated therein.

Embodiments of the present invention may be operational with numerous general-purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 120 includes a general-purpose computing device in the form of a control server 122. Components of the control server 122 may include, without limitation, a processing unit, internal system memory, and a suitable system bus for coupling various system components, including database cluster 124, with the control server 122. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 122 typically includes therein, or has access to, a variety of computer-readable media, for instance, database cluster 124. Computer-readable media can be any available media that may be accessed by server 122, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 122. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 124, provide storage of computer-readable instructions, data structures, program modules, and other data for the control server 122. The control server 122 may operate in a computer network 126 using logical connections to one or more remote computers 128. Remote computers 128 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 128 may also be physically located in non-traditional medical care environments so that the entire health care community may be capable of integration on the network. The remote computers 128 may be personal computers, servers, routers, network PCs, peer devices, other common network nodes, or the like, and may include some or all of the elements described above in relation to the control server 122. The devices can be personal digital assistants or other like devices.

Exemplary computer networks 126 may include, without limitation, local area networks (LANs) and/or wide area networks (WANs). Such networking environments are commonplace in offices, enterprise-wide computer networks, intranets, and the Internet. When utilized in a WAN networking environment, the control server 122 may include a modem or other means for establishing communications over the WAN, such as the Internet. In a networked environment, program modules or portions thereof may be stored in association with the control server 122, the database cluster 124, or any of the remote computers 128. For example, and not by way of limitation, various application programs may reside on the memory associated with any one or more of the remote computers 128. It will be appreciated by those of ordinary skill in the art that the network connections shown are exemplary and other means of establishing a communications link between the computers (e.g., control server 122 and remote computers 128) may be utilized.

In operation, a clinician may enter commands and information into the control server 122 or convey the commands and information to the control server 122 via one or more of the remote computers 128 through input devices, such as a keyboard, a pointing device (commonly referred to as a mouse), a trackball, or a touch pad. Other input devices may include, without limitation, microphones, scanners, or the like. Commands and information may also be sent directly from a remote healthcare device to the control server 122. In addition to a monitor, the control server 122 and/or remote computers 128 may include other peripheral output devices, such as speakers and a printer.

Although many other internal components of the control server 122 and the remote computers 128 are not shown, those of ordinary skill in the art will appreciate that such components and their interconnection are well known. Accordingly, additional details concerning the internal construction of the control server 122 and the remote computers 128 are not further disclosed herein.

Figure 2:
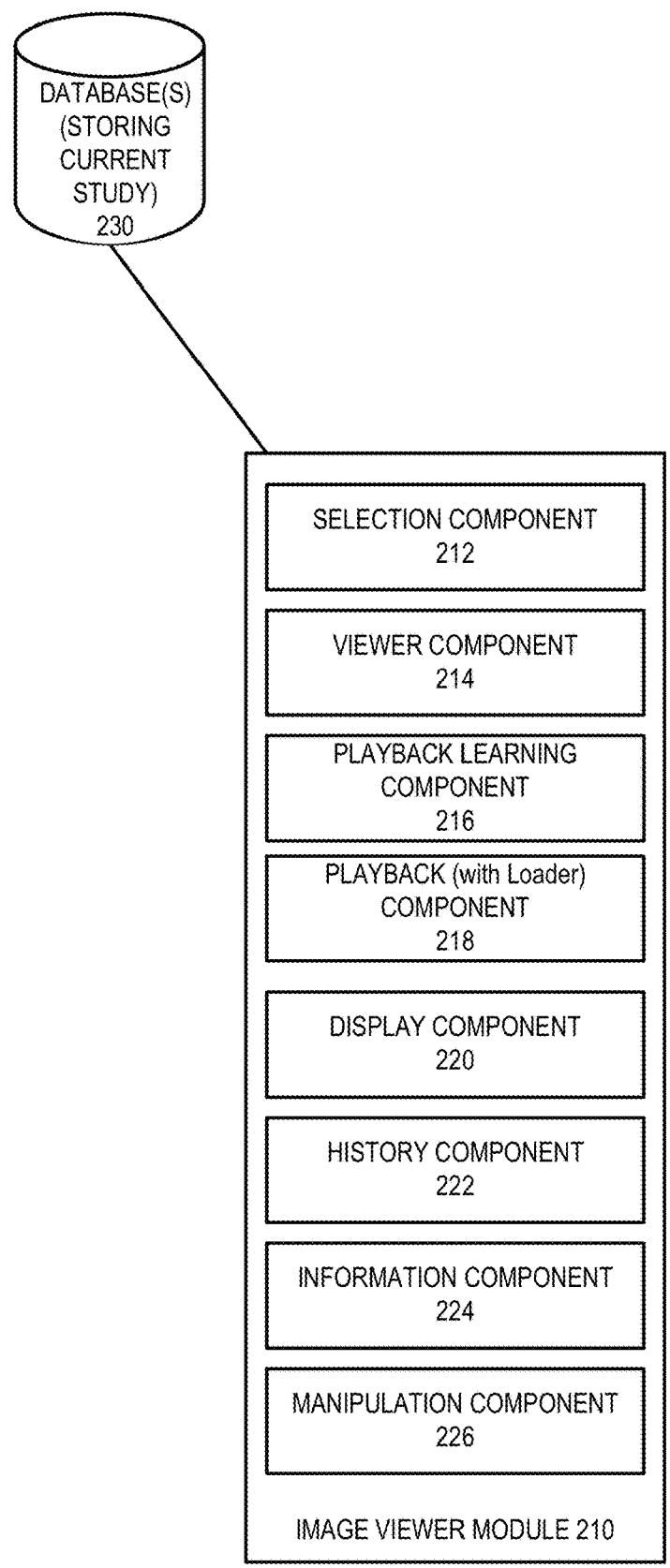
FIG. 2 is a block diagram showing one embodiment of a computing system architecture for displaying series images in a graphical user interface (GUI).

With reference to FIG. 2, a block diagram is illustrated that shows an exemplary computing system architecture for seamless viewing of medical images (e.g., DICOM images) in a low network speed environment by locally rendering images using compressed image pixel data cached locally. It will be appreciated that the computing system architecture shown in FIG. 2 is merely an example of one suitable computing system and is not intended as having any dependency or requirement related to any single module/component or combination of modules/components.

The computing system includes an image viewer 210 and one or more databases 230, storing and maintaining medical images from image series of multiple healthcare studies. Exemplary medical images include radiology images, laboratory images, pictures, cardiology images, such as ECHO images, and other healthcare images. One of skill in the art will appreciate that the databases may be maintained separately or may be integrated. Databases 230 may contain images that are linked to a patient's electronic medical record (EMR), such that images may be selected from within the EMR and launched and displayed within a viewer via the image viewer 210. As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); other images; evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare. Display component 220 includes a graphical display device that may be a monitor, computer screen, project device or other hardware device for displaying output capable of displaying graphical user interfaces.

Image viewer 210 receives and displays images that are sourced from more than one source, or database. Thus, a single storage repository or a single PACS system is not required. Image viewer 210 may reside on one or more computing devices, such as, for example, the control server 122 described above with reference to FIG. 1. By way of example, the control server 122 includes a computer processor and may be a server, personal computer, desktop computer, laptop computer, handheld device, mobile device, consumer electronic device, or the like.

Image viewer 210 comprises selection component 212, viewer component 214, playback learning component 216, playback component 218, and display component 220. In various embodiments, image viewer 210 includes a history component 222, an information component 224, and a manipulation component 226. It will be appreciated that while image viewer 210 is depicted as receiving healthcare images from a current study stored in database 230, image viewer 210 may receive healthcare images from multiple sources including databases spread across multiple facilities and/or multiple locations. It will also be appreciated that image viewer 210 may receive healthcare images from the sources described above via links within a patient's EMR.

The selection component 212 receives a selection of a healthcare study. A healthcare study comprises one or more series. Each series comprises one or more images depicting the subject of the image from various angles. A list perspective within a multimedia manager provides a list of available studies, images, and other media. A clinician can select the desired items to launch in the viewer. In one embodiment, the selection of desired items may be made within the EMR.

Once the selection component 212 receives the clinician's selection, the viewer component 214 launches the viewer for the selected studies or series. These images may be cine images or other medical images. Playback component 218 playbacks images of the selected studies using the view of viewer component 214 according to a playback behavior, thereby allowing a user to smoothly scroll the images. In one embodiment, playback component 218 fetches displayable images from memory (e.g., a local cache) and draws the images in a viewport of the viewer. The display component 220 displays the one or more images of the current study or series in the viewer.

Playback learning component 216 receives user inputs (e.g., mouse movements) from the user during playback and uses those inputs with other historical user inputs to update the playback behavior. In one embodiment, this update occurs while the user is viewing the images during playback.

In one embodiment, a history component 222 displays a history of different studies and clinical images associated with the more than one healthcare image. The history component 222 further allows a selection of one or more images from the history to be displayed in the viewer by the display component 220. For example, the selection component 212 may have received a selection from the clinician of a particular study. However, once the display component 220 has displayed the images that comprise that selected study, the history component 222 may display other studies and clinical images that are of particular interest to the clinician. The clinician may then select additional items from the history to launch within the viewer.

In one embodiment, information component 224 displays additional information associated with the more than one healthcare image, the history, or a combination thereof. The additional information comprises patient identifying information, image related information, study related information, or a combination thereof. Such additional information may also include time related information.

In one embodiment, a manipulation component 226 allows a clinician to manipulate a display of a healthcare image. For example, a clinician may determine that the image as it is rendered within the viewer is not large enough to see a desired level of detail. The clinician may zoom in or out and the manipulation component 226 manipulates the display of the image accordingly. Similarly, the clinician may desire to pan an image and the manipulation component 226 manipulates the image display accordingly.

Figure 3:
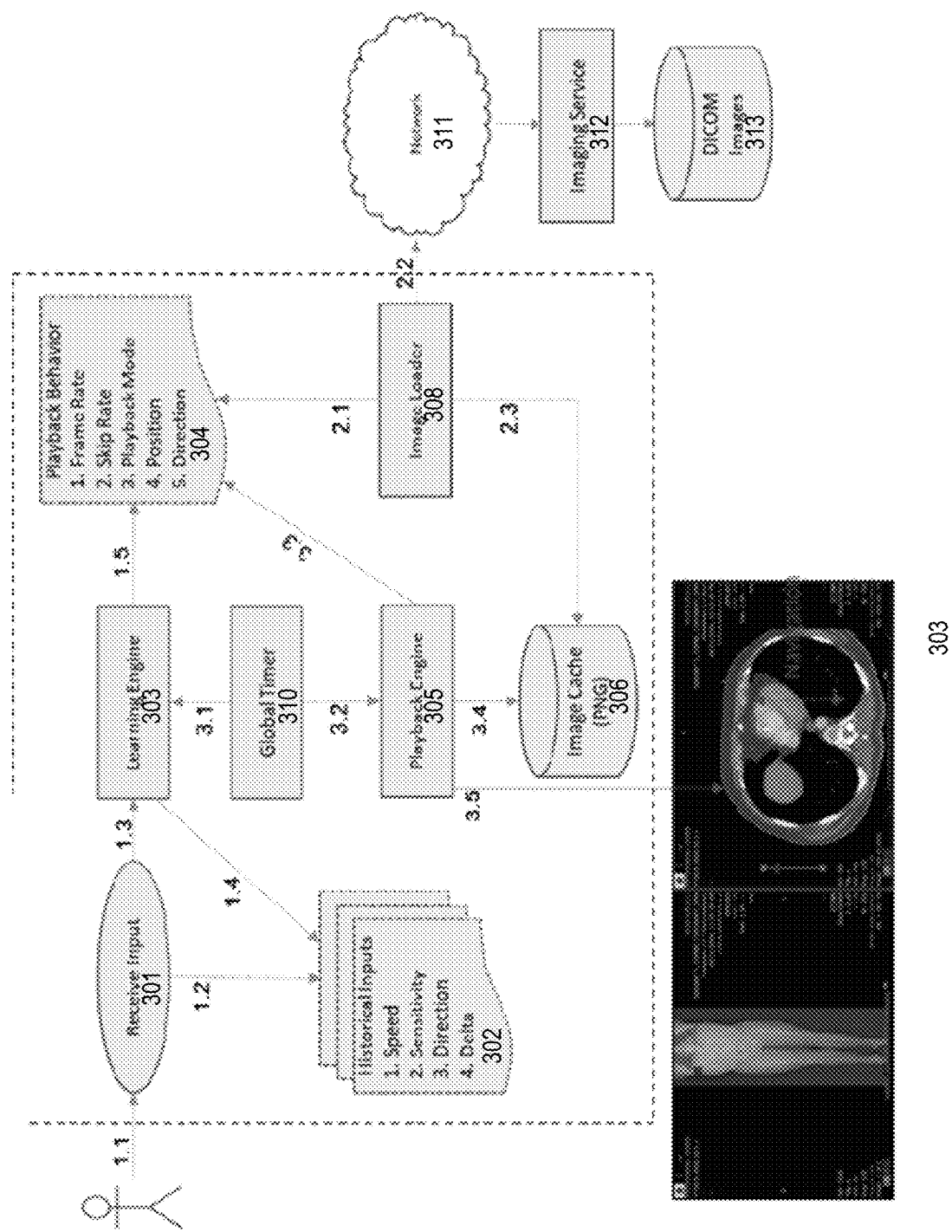
FIG. 3 is a data flow diagram of one embodiment of a process for image rendering being performed with a medical image management system.

FIG. 3 is a data flow diagram of one embodiment of a process for image rendering being performed with a medical image management system. The medical image management system performs image rendering and viewing to create a layout in the GUI with at least one image from one image series of the current study. In one embodiment, the medical image management system provides seamless viewing of medical images (e.g., DICOM images) in low network speed environment by caching compressed image pixel data in the system and rendering images locally. In one embodiment, the system is implemented with one of the viewers of FIG. 2 or the system of FIG. 7.

In one embodiment, the medical image management system comprises a network communication interface to receive images of a healthcare study; an image cache memory to cache the images; one or more processors coupled to the network connection interface and the memory and configured to dynamically change playback behavior for navigating through images of the healthcare study based on analyzing historical user inputs made with one or more user input devices while a user is navigating through the images; and a display coupled to the one or more processors to display the images in a viewport or other graphical user interface (GUI). In one embodiment, the processors change the navigation speed and direction of the playback behavior while images are being reviewed by a user. In one embodiment, this change in the playback behavior occurs seamlessly while the user scrolls through the images. In one embodiment, the processors implement a learning engine to derive the playback behavior for navigating through images based on analyzing historical user inputs made with one or more user input devices and a playback engine to perform playback of images according to the playback behavior, wherein the display is operable to display the images with the viewer under direction of the playback engine.

Referring to FIG. 3, in one embodiment, the process for image rendering being performed with the medical image management system has three logical parts.
1. A Learning Engine 303: Learn from historical inputs (from user input devices (e.g., mouse or other cursor control movements, touchscreen inputs, keyboard inputs, etc.) and derive playback behavior 304.
2. An Image Loader 308: Pre-fetch and cache displayable images (e.g., DICOM images) from an imaging service 312 (e.g., a remotely located server(s), etc.), where the prefetching in one embodiment is through a Web Access to DICOM Objects (WADO) interface from imaging service 312.
3. A Playback Engine 305: Seamless playback through DICOM images.

One embodiment of the operations associated with part is depicted in FIG. 4. As shown in FIG. 4, and described in more detail below, operations numbered 1.1-1.5 in FIGS. 3 and 4 are associated with learning engine 303 and include receiving input from the user [1.1], storing input attributes to history 302 [1.2], notifying learning engine 303 of the arrive of user inputs [1.3], learning engine 303 fetching historical input attributes [1.4], and learning engine 303 creation and/or updating playback behavior 304 [1.5]. Similarly, operations numbered 2.1-2.3 in FIGS. 3 and 4 are associated with image loader 308 and include image loader 308 fetching playback behavior 304 [2.1], image loader 308 performing a request (e.g., a WADO request) to imaging service 312 [2.2], and image loader 308 caching displayable images into cache 306 [2.3] Lastly, operations numbered 3.1-3.5 in FIGS. 3 and 4 are associated with playback engine 305 and include synchronizing user inputs 301 and playback engine 305 [3.1], [3.2], playback engine 305 fetching playback behavior 304 [3.3], playback engine 304 fetching one or more displayable images from cache 306 [3.4], and playback engine 304 drawing one or more images in the viewport [3.5]. These operations are described in more detail below.

Referring both FIGS. 3 and 4, the system receives one or more user inputs 301 made by a user viewing images with the medical image management. These user inputs are made with user input devices such as, for example, but not limited to, a mouse or other cursor control device, a touchscreen displaying graphical user interface (GUI) elements, keyboard. The user inputs are stored in a memory (302).

Learning engine 303 is notified of and receives user inputs (301). In one embodiment, the inputs are received by learning engine 303 continuously. The learning engine caches attributes of user input into memory 302. In one embodiment, in the case of a mouse, the attributes of the user inputs that are stored are speed of mouse movement, mouse sensitivity, direction of movement, and the delta (or the distance between adjacent mouse movements), which is the total amount of physical distance (e.g., total movement in x and y directions) between the previous movement and the current movement.

Learning engine 303 fetches the most recent historical inputs from memory and analyzes them together with image information (e.g., DICOM image information). In one embodiment, the image information comprises the modality that created the image and other images in the study or series or the type of images, the number of image instances (e.g., a large number of images such as with a full body scan (e.g., 1000 images), a small number of images (e.g., 4 to 8 images, etc.), patient position and direction vectors (e.g., a combination of image plane and view position of the 3D volume though which user is navigating, etc.). In one embodiment, learning engine 303 interprets the user intention from the analysis and translates it into playback behavior 304 which consists of attributes defining playback behavior (304). In one embodiment, attributes of playback behavior 304 include one or more of frame rate, skip rate, playback mode, patient position and direction vector. The frame rate is the frequency at which the images are displayed in the sequence. The skip rate is the rate at which frames are skipped, which may depend on the frame rate and the ability of the human eye to visualize frames when the navigation through the frames is occurring at certain speeds. The playback mode refers to the manner in which the user is navigating through the images (e.g., proceeding to a couple of images in the middle of the study first and then going back to an earlier image). Patient position is the area to which the user is moving. The direction refers to the direction vectors which are a combination of image plane and view position of the 3D volume though which user is navigating. In one embodiment, the playback behavioral attributes include all of these attributes. In other words, learning engine 303 dynamically modifies playback behavior 304 used to display images of a study or series. In one embodiment, this dynamic change or modification occurs while the user is viewing images from the study or series. That is, the modification occurs while the playback is occurring.

For example, in one embodiment, learning engine 303 determines that the user's mouse movements have increase in speed and interprets this to mean that the user desires to increase the navigation speed while navigating through the images. Thus, learning engine 303 increases the frame rate, which may mean the skip rate is increased to maintain that frame rate. The skip rate might also be increased because the user is moving very quickly with the mouse from one area to the next. In another example, while the user is interacting with the images, the inputs associated with those movements are being recorded, such as how fast the user moved the mouse to move through the images, and the direction of those movements (e.g., back and forth through some of the images, etc.) and, from these and other historical inputs and image information, the learning engine derives a behavior. In one embodiment, each of these factors causes the navigation to be changed. For example, in the case of the number of image instances, the skip rate is determined based on number of images in the series; and for a smaller size series, the rate of skip is also small. With respect to the modality, for example, MG images are required to be aligned with the breast bounding box by loading additional bounding box information from server during navigation. In the case of the type of image, for example, larger images require pre-fetch for smooth scrolling and images with spatial information require spatial synchronization with other viewports. With respect to patient position, for example, the skip rate is decided based on adjacent patient positions where slices having large spatial position difference are navigated without skipping images. In the case of direction vectors, for example, a 3D volume requires direction vectors to decide the playback direction based on the plane and user's view direction. Thus, each of these can influence the playback behavior and the learning engine 303 is able to determine playback behavior 304 based on these factors.

Playback behavior 304 is used by both an image loader 308 that is responsible for loading images into a memory of the medical image management system and by playback engine 305 that plays back images to the user according to playback behavior 304. In one embodiment, image loader 308 loads images for playback so that the images are available in displayable format in the cache well ahead in order facilitate seamless playback without having to stop due to image unavailability. Image loader 308 accesses playback behavior 304 and uses it to determine which images to cache. In one embodiment, image loader 308 sends requests for images via a network interface of the medical image management system over network 311 (e.g., the Internet). In one embodiment, image loader 308 sends the request as a Web Access to DICOM Objects (WADO) request to an imaging service 312 for retrieving rendered displayable images (e.g., DICOM images). In one embodiment, imaging service 312 is at a remotely located server, receives the request from network 311 and fetches the image images from DICOM image storage 313. After fetching image, imaging service 312 renders the image pixel data into images. After rendering, the rendered images are sent back to the medical image management system via network 311 where they are received by the management system's network interface and cached in image cache 306 by image loader 308 so that they are available for display during user navigation. Thus, image loader 308 operates in accordance with playback behavior 304 composed by learning engine 303 in order to make sure the images intended for display will always available for playback.

Playback engine 305 focuses on continuous and smooth playback navigation through images based on playback behavior 304 composed by learning engine 303. In one embodiment, playback engine 305 access playback behavior 304 and fetches displayable images from cache memory 306 and draws each image in the viewport or other GUI for display on the display of the medical image management system. In one embodiment, playback engine 305 also makes sure, quick interactive stop or start in navigation by radiologist or other medical personnel at specific slice will be honored.

In one embodiment, a global timer 310 controls playback engine 305. Global timer 310 synchronizes the user inputs 301 and playback engine 305, which enables learning engine 303 to be synchronized with playback engine 305.

Figure 5:
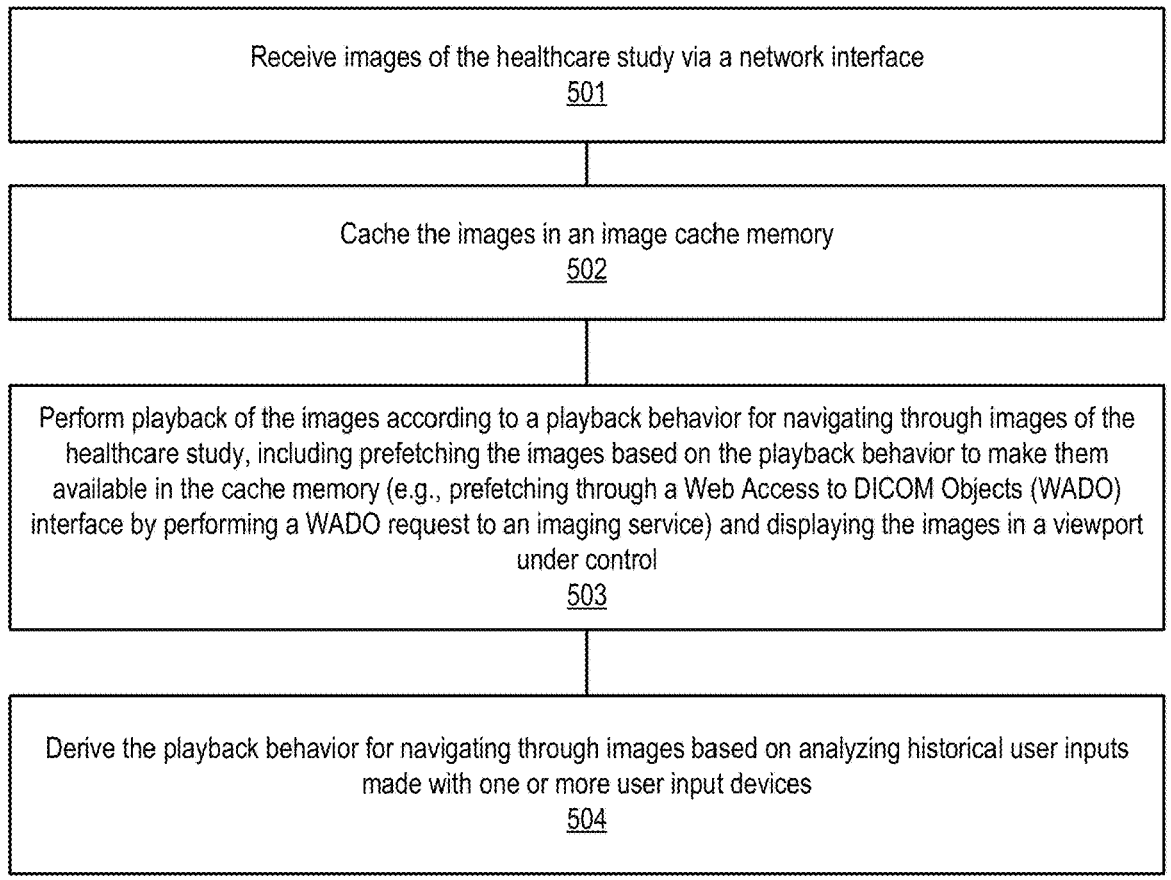
FIG. 5 is a flow diagram of one embodiment of a process for displaying images in a graphical user interface (GUI).

FIG. 5 is a flow diagram of one embodiment of a process for displaying series images in a graphical user interface (GUI). In one embodiment, the processes are performed by processing logic that may comprise hardware (circuitry, dedicated logic, etc.), software (e.g., software running on a chip), firmware, or a combination of the three. In one embodiment, the process is performed by a medical image management system having an image processor, an image renderer, and a display.

Referring to FIG. 5, the process begins by processing logic receiving images of the healthcare study via a network interface (processing block 501) and caching the images in an image cache memory (processing block 502). In one embodiment, the images are part of healthcare studies. In one embodiment, the images are received from an imaging service that is remote to the medical image management system.

Once images have been received, processing logic performs playback of the images according to a playback behavior for navigating through images of the healthcare study, including prefetching the images based on the playback behavior to make them available in the cache memory (e.g., prefetching through a Web Access to DICOM Objects (WADO) interface by performing a WADO request to an imaging service) and displaying the images in a viewport under control (processing block 503).

Figure 6:
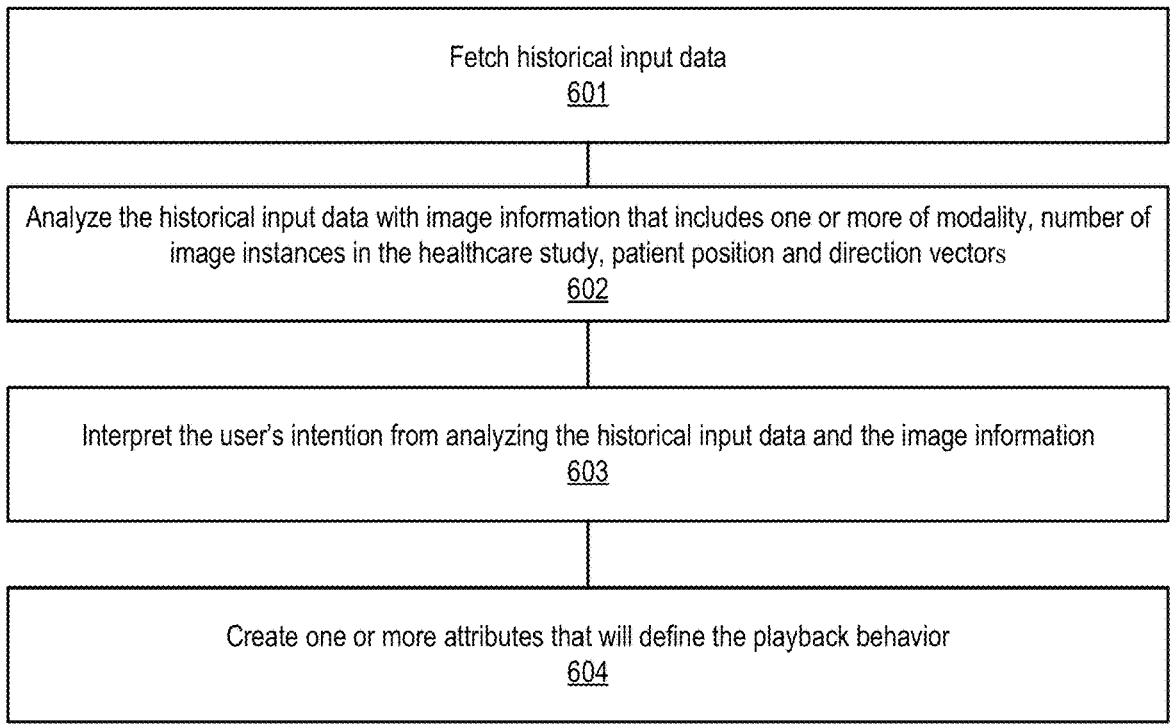
FIG. 6 is a flow diagram of one embodiment of a process for deriving the playback behavior for navigating through images based on analyzing historical user inputs made with one or more user input devices.

In one embodiment, while performing playback of the images, processing logic derives the playback behavior for navigating through images based on analyzing historical user inputs made with one or more user input devices (processing block 504). FIG. 6 is a flow diagram of one embodiment of a process for deriving the playback behavior for navigating through images based on analyzing historical user inputs made with one or more user input devices. In one embodiment, the processes are performed by processing logic that may comprise hardware (circuitry, dedicated logic, etc.), software (e.g., software running on a chip), firmware, or a combination of the three. In one embodiment, the process is performed by a medical image management system having a playback learning engine, a playback engine, and a display. Referring to FIG. 6, the process begins by fetching historical input data (processing block 601). In one embodiment, the historical input data comprises one or more of speed of mouse movement, mouse sensitivity, direction of movement, and delta. In one embodiment, the historical data comprises all of these inputs. Next, processing logic analyzes the historical input data with image information that includes one or more of modality, number of image instances in the healthcare study, patient position and direction vectors (processing block 602) and interprets the user's intention from analyzing the historical input data and the image information (processing block 603). Using the interpreted user intention, processing logic creates one or more attributes that will define the playback behavior (processing block 604). That is, the attributes set the playback to occur in a particular way. In one embodiment, the attributes comprise one or more of frame rate, skip rate, playback mode, patient position and direction vector.

Returning to FIG. 5, after deriving the playback behavior, processing logic dynamically changes the playback behavior based on analyzing historical user inputs made with one or more user input devices while a user is navigating through the images. In one embodiment, dynamically changing the playback behavior comprises changing navigation speed and direction of the playback behavior while images are being reviewed by a user. In one embodiment, dynamically changing the playback behavior occurs seamlessly while the user scrolls through the images.

An Exemplary Medical Imaging Management System

Figure 7:
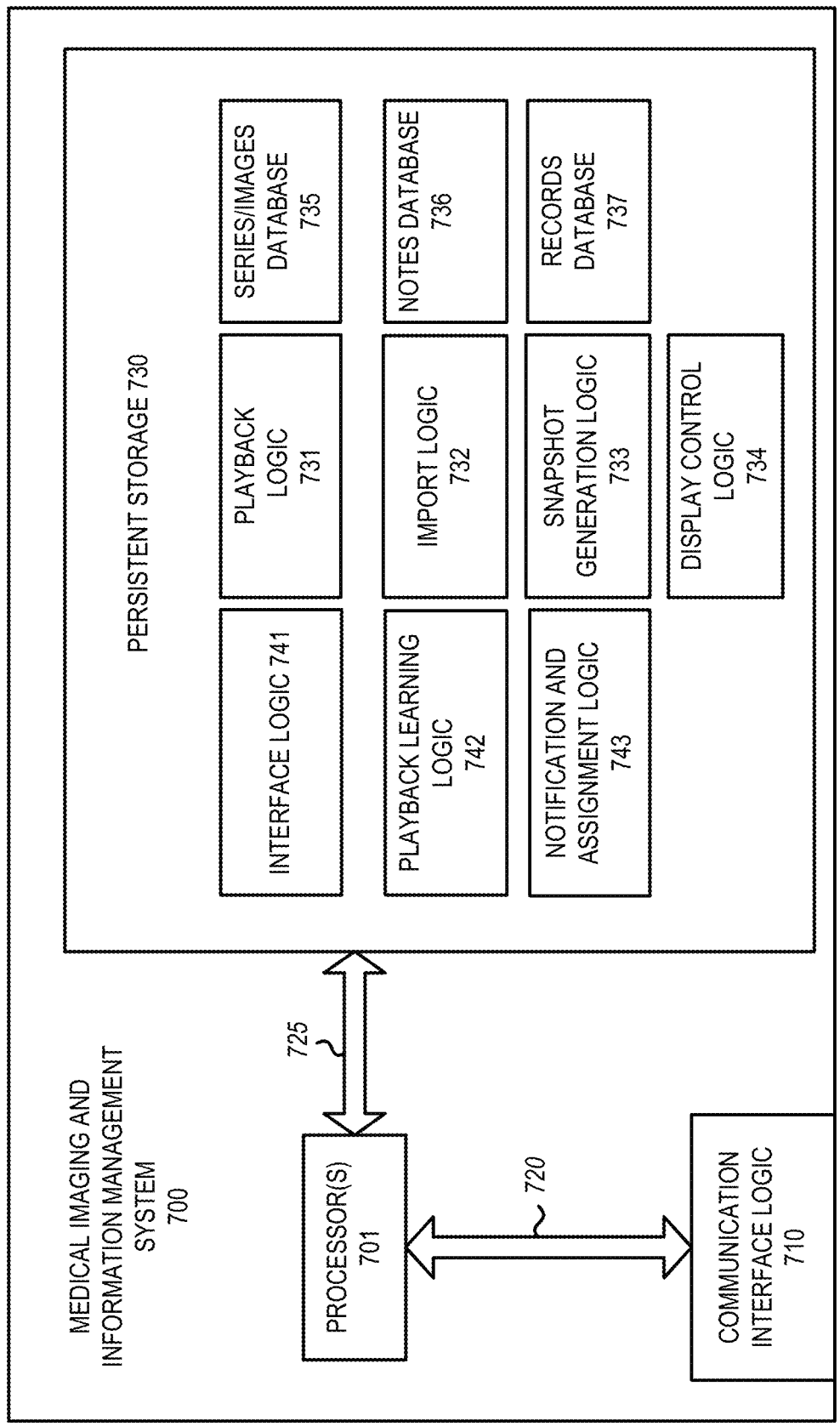
FIG. 7 illustrates an exemplary embodiment of a logical representation of a medical imaging and information management system that generates and renders images from healthcare studies.

FIG. 7 illustrates an exemplary embodiment of a logical representation of a medical imaging and information management system 700 that generates and renders image comparison layouts discussed above. The system performs matching of image series based on image similarity and automatically creates layouts with series images of a current study and one or more past (previously-created) studies. In one embodiment, system 700 is part of a medical image system such as detailed above.

The medical imaging and information management system 700 includes one or more processors 701 that are coupled to communication interface logic 710 via a first transmission medium 720. The communication interface logic 710 enables communications with other electronic devices, specifically enabling communication with remote users such as doctors, nurses and/or medical technicians, remote databases (e.g., PACS) that store healthcare studies, and healthcare modalities that generate and send studies. According to one embodiment of the disclosure, communication interface logic 710 may be implemented as a physical interface including one or more ports for wired connectors. Additionally, or in the alternative, communication interface logic 710 may be implemented with one or more radio units for supporting wireless communications with other electronic devices.

The processor(s) 701 is further coupled to persistent storage 730 via transmission medium 725. According to one embodiment of the disclosure, persistent storage 730 may include (a) user interface logic 741, (b) playback learning logic 742, (c) notification and assignment logic 743, (d) playback logic 731, (e) an import logic 732, (f) a snapshot generation logic 733, (g) a display control logic 734, (h) an images database 735, (i) a notes database 736 and (j) a records database 737.

The user interface logic 741 may include logic for enabling interaction between a user and the display areas being displayed on the screen.

The playback learning logic 742 includes logic for accessing historical user inputs used when navigating images of a series or study and modifying the playback behavior used by the system to navigate the images based on the learned user behavior.

Notification and assignment logic 743 includes logic to issue and send notifications and/or assignments for study reviews.

Playback logic 742, in cooperation with display control logic 734, controls the playback of the images according to playback behavior stored in the system. Playback logic 742 accesses the playback behavior and, based on the playback behavior, fetches displayable images from the cache memory and drawings images in the viewport. In one embodiment, playback logic 742 operates in conjunction with loader logic that obtains images from remote locations and stores them in a cache memory in system 700 so that they may be viewed during playback in a seamless manner.

Import logic 732 may include logic for retrieving one or more pieces of information from a storage device and importing each of the one or more pieces of information into a separate display area of a viewer or viewer template. For example, the pieces of information may include, but are not limited or restricted to, (i) medical images, including x-rays, mammograms, computerized tomography (CT) scans, magnetic resonance imaging (MM), positron emission tomography (PET) scan and/or ultrasound imaging, (ii) physician's notes regarding one or more of the medical images and/or (iii) medical records corresponding to one or more of the subjects of the one or more medical images.

The snapshot generation logic 733 includes logic for saving at least a first state of the layout template. Saving the first state may include storing, at least, (i) the one or more pieces of information, and (ii) viewing properties of each of the one or more pieces of information in a non-transitory computer-readable medium. The layout template may depict a comparison layout depicting one or more images from a current study and one or more images determined to be similar from one or more previously-created studies.

The display control logic 734 includes logic for displaying images that have been rendered locally from the compressed image pixel data or have been rendered server-side and sent from the server in displayable form. In one embodiment, the display control logic 734 includes logic to display a browser into which the images are displayed.

The images database 735, the notes database 736 and the records database 737 may comprise a single non-transitory computer-readable medium storage device or may each be a separate non-transitory computer-readable medium storage device. The images database 735 stores medical images that a user may import into a display area of a viewer or other GUI. The notes database 736 stores notes recorded by a doctor, nurse, medical technician, etc., that a user may import into a display area of a layout template. Finally, the records database 737 stores medical records that a user may import into a display area of a layout template.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A system comprising:
   a network communication interface to receive images of a healthcare study;
   an image cache memory to cache the images;
   a display coupled to one or more processors to display the images in a viewport; and
   the one or more processors coupled to a network communication interface and the memory and configured to dynamically change one or more of frame rate, skip rate, playback mode, patient position and direction vector, as playback behavior for navigating through images of the healthcare study based on analyzing historical user inputs made with one or more user input devices while a user is navigating through the images, wherein the one or more processors implement:
      a learning engine to derive the playback behavior for navigating through images based on analyzing historical user inputs made with one or more user input devices, wherein deriving the playback behavior by the learning engine comprises:
         fetching historical input data and updating the playback behavior, wherein the historical input data comprises one or more of speed of mouse movement, mouse sensitivity, direction of movement through the images, and distance between adjacent mouse movements;
         analyzing the historical input data with image information that includes one or more of modality, number of image instances in the healthcare study, patient position and direction vectors;
         interpreting user intention from analyzing the historical input data and the image information; and
         creating one or more attributes based on the interpretation, the attributes defining the playback behavior; and
      a playback engine to perform playback of images according to the playback behavior, wherein the display is operable to display the images with the viewer under direction of the playback engine.

2. The system defined in claim 1, wherein at least one processor of the one or more processors is operable to change navigation speed and direction of the playback behavior while images are being reviewed by a user.

3. The system defined in claim 2, wherein change in the playback behavior occurs seamlessly while the user scrolls through the images.

4. The system defined in claim 1, wherein the one or more attributes comprise one or more of the frame rate, the skip rate, the playback mode, the patient position and the direction vector.

5. The system defined in claim 1, wherein the playback engine is operable to fetch the playback behavior, fetch displayable images from the image cache based on the playback behavior, and draw each of the images in the viewport.

6. The system defined in claim 1, wherein the one or more processors implement an image loader operable to fetch the playback behavior, prefetch and cache the images based on the playback behavior, make them available in the cache memory.

7. The system defined in claim 6, wherein the image loader is operable to prefetch the images through a Web Access to DICOM Objects (WADO) interface by performing a WADO request to an imaging service.

8. The system defined in claim 7, wherein imaging service is at a server remotely located with respect to the system and the WADO request is made via the network connection.

9. The system defined in claim 1, wherein the viewport is part of a browser.

10. A method for displaying images from a healthcare study in a graphical user interface (GUI), the method comprising:
   receiving images of the healthcare study via a network interface;
   caching the images in an image cache memory;
   deriving a playback behavior for navigating through images based on analyzing historical user inputs made with one or more user input devices, wherein deriving the playback behavior comprises fetching historical input data and updating the playback behavior, wherein the historical input data comprises one or more of speed of mouse movement, mouse sensitivity, direction of movement through the images, and distance between adjacent mouse movements, wherein deriving the playback behavior further comprises:
      analyzing the historical input data with image information that includes one or more of modality, number of image instances in the healthcare study, patient position and direction vectors;
      interpreting user intention from analyzing the historical input data and the image information; and
      creating one or more attributes based on the interpretation, the attributes defining the playback behavior;
   performing playback of the images according to the playback behavior for navigating through images of the healthcare study, including displaying the images in a viewport under control; and dynamically changing one or more of frame rate, skip rate, playback mode, patient position and direction vector in the playback behavior based on analyzing the historical user inputs.

11. The method defined in claim 10, wherein dynamically changing the playback behavior comprises changing navigation speed and direction of the playback behavior while images are being reviewed by a user.

12. The method defined in claim 11, wherein dynamically changing the playback behavior occurs seamlessly while the user scrolls through the images.

13. The method defined in claim 10, wherein the one or more attributes comprise one or more of the frame rate, the skip rate, the playback mode, the patient position and the direction vector.

14. The method defined in claim 10, further comprising: fetching the playback behavior and prefetching the images based on the playback behavior to make them available in the cache memory through a Web Access to DICOM Objects (WADO) interface by performing a WADO request to an imaging service.

15. A non-transitory computer readable storage media having instructions stored thereupon which, when executed by a system having at least a processor and a memory therein, cause the system to perform a method for displaying images from a healthcare study in a graphical user interface (GUI), wherein the method comprises:
    receiving images of the healthcare study via a network interface;
    caching the images in an image cache memory;
    deriving a playback behavior for navigating through images based on analyzing historical user inputs made with one or more user input devices, wherein deriving the playback behavior comprises fetching historical input data and update the playback behavior, wherein the historical input data comprises one or more of speed of mouse movement, mouse sensitivity, direction of movement through the images, and distance between adjacent mouse movements;
    performing playback of the images according to the playback behavior for navigating through images of the healthcare study, including displaying the images in a viewport under control;
    dynamically changing one or more of frame rate, skip rate, playback mode, patient position and direction vector in the playback behavior based on analyzing the historical user inputs;
    fetching historical input data and update the playback behavior, wherein the historical input data comprises one or more of speed of mouse movement, mouse sensitivity, direction of movement, and delta; analyzing the historical input data with image information that includes one or more of modality, number of image instances in the healthcare study, patient position and direction vectors; and
    interpreting user intention from analyzing the historical input data and the image information; and creating one or more attributes based on the interpretation, the attributes defining playback behavior.

16. The computer readable storage media defined in claim 15, wherein dynamically changing the playback behavior comprises changing navigation speed and direction of the playback behavior while images are being reviewed by a user.

17. The computer readable storage media defined in claim 16, wherein dynamically changing the playback behavior occurs seamlessly while the user scrolls through the images.

18. The computer readable storage media defined in claim 15, wherein the method further comprises deriving the playback behavior for navigating through images based on analyzing historical user inputs made with one or more user input devices.

19. The computer readable storage media defined in claim 15, wherein the one or more attributes comprise one or more of the frame rate, the skip rate, the playback mode, the patient position and the direction vector.

20. The computer readable storage media defined in claim 15, wherein the method further comprises fetching the playback behavior and prefetching the images based on the playback behavior to make them available in the cache memory through a Web Access to DICOM Objects (WADO) interface by performing a WADO request to an imaging service.

* * * * *